(12) United States Patent
Tang et al.

(10) Patent No.: US 8,383,852 B2
(45) Date of Patent: Feb. 26, 2013

(54) COMPOUNDS HAVING A CYCLIC MOIETY AND COMPOSITIONS FOR DELIVERING ACTIVE AGENTS

(75) Inventors: Pingwah Tang, Elmsford, NY (US); Steven Dinh, Briarcliff Manor, NY (US)

(73) Assignee: Emisphere Technologies, Inc., Cedar Knolls, NJ (US)

( * ) Notice: Subject to any disclaimer, the term of this patent is extended or adjusted under 35 U.S.C. 154(b) by 485 days.

(21) Appl. No.: 12/527,221

(22) PCT Filed: Feb. 19, 2008

(86) PCT No.: PCT/US2008/054245
§ 371 (c)(1),
(2), (4) Date: Aug. 14, 2009

(87) PCT Pub. No.: WO2008/101240
PCT Pub. Date: Aug. 21, 2008

(65) Prior Publication Data
US 2010/0074861 A1    Mar. 25, 2010

Related U.S. Application Data

(60) Provisional application No. 60/890,458, filed on Feb. 16, 2007.

(51) Int. Cl.
*A01N 35/00* (2006.01)
*A61K 31/12* (2006.01)

(52) U.S. Cl. ......... 562/465; 562/466; 562/470; 562/471

(58) Field of Classification Search .................. None
See application file for complete search history.

(56) References Cited

U.S. PATENT DOCUMENTS

| | | |
|---|---|---|
| 5,401,516 A | 3/1995 | Milstein et al. |
| 5,443,841 A | 8/1995 | Milstein et al. |
| 5,629,020 A | 5/1997 | Leone-Bay et al. |
| 5,643,957 A | 7/1997 | Leone-Bay et al. |
| 5,766,633 A | 6/1998 | Milstein et al. |
| RE35,862 E | 7/1998 | Steiner et al. |
| 5,776,888 A | 7/1998 | Leone-Bay et al. |
| 5,866,536 A | 2/1999 | Leone-Bay et al. |
| 2005/0119502 A1 | 6/2005 | Gschneidner et al. |

FOREIGN PATENT DOCUMENTS

WO    0040203 A2    7/2000

OTHER PUBLICATIONS

Lee et al. Letters in drug design & discovery, 2004, 1(1), 19-23.*
Hirth et al Bioorganic and Medicinal Chemistry Letters, 2005, 15, 2087-2091.*

* cited by examiner

*Primary Examiner* — Yevegeny Valenrod
(74) *Attorney, Agent, or Firm* — Blank Rome LLP

(57) ABSTRACT

Compounds comprising cyclic moiety and compositions for the delivery of active agents are provided. Methods of administration and preparation are provided as well.

10 Claims, No Drawings

COMPOUNDS HAVING A CYCLIC MOIETY AND COMPOSITIONS FOR DELIVERING ACTIVE AGENTS

CLAIM OF PRIORITY

This application is a U.S. national phase under 35 U.S.C. §371 of International Patent Application No. PCT/US08/54245 filed Feb. 19, 2008, which claims priority under 35 U.S.C. §119(e) to U.S. Provisional Application No. 60/890,458, filed Feb. 16, 2007, which is incorporated by reference herein in its entirety. The International Application was published in English on Aug. 21, 2008 as WO 2008/101240.

FIELD OF THE INVENTION

The present invention relates to delivery agent compounds comprising a cyclic moiety. These compounds are useful for delivering active agents, such as biologically or chemically active agents, to an animal (e.g. a human). Methods for the preparation and administration of such compositions are also disclosed.

BACKGROUND OF THE INVENTION

Conventional means for delivering active agents are often severely limited by biological, chemical and physical barriers. Typically, these barriers are imposed by the environment through which delivery occurs, the environment of the target for delivery, and/or the target itself. Biologically and chemically active agents are particularly vulnerable to such barriers.

In the delivery to animals of biologically active and chemically active pharmacological and therapeutic agents, barriers are imposed by the body. Examples of physical barriers are the skin, lipid bi-layers and various organ membranes that are relatively impermeable to certain active agents but must be traversed before reaching a target, such as the circulatory system. Chemical barriers include, but are not limited to, pH variations in the gastrointestinal (GI) tract and degrading enzymes.

These barriers are of particular significance in the design of oral delivery systems. Oral delivery of many biologically or chemically active agents would be the route of choice for administration to animals if not for biological, chemical, and physical barriers. Among the numerous agents which are not typically amenable to oral administration are biologically or chemically active peptides, such as calcitonin and insulin; polysaccharides, and in particular mucopolysaccharides including, but not limited to, heparin; heparinoids, antibiotics, and other organic substances. These agents may be rapidly rendered ineffective or destroyed in the gastro-intestinal tract by acid hydrolysis, enzymes, and the like. In addition, the size and structure of macromolecular drugs may prohibit absorption.

Earlier methods for orally administering vulnerable pharmacological agents have relied on the co-administration of adjuvants (e.g., resorcinols and non-ionic surfactants such as polyoxyethylene oleyl ether and n-hexadecylpolyethylene ether) to increase artificially the permeability of the intestinal walls, as well as the co-administration of enzymatic inhibitors (e.g., pancreatic trypsin inhibitors, diisopropylfluorophosphate (DFF) and trasylol) to inhibit enzymatic degradation. Liposomes have also been described as drug delivery systems for insulin and heparin. However, broad spectrum use of such drug delivery systems is precluded because: (1) the systems require toxic amounts of adjuvants or inhibitors; (2) suitable low molecular weight cargos, i.e. active agents, are not available; (3) the systems exhibit poor stability and inadequate shelf life; (4) the systems are difficult to manufacture; (5) the systems fail to protect the active agent (cargo); (6) the systems adversely alter the active agent; or (7) the systems fail to allow or promote absorption of the active agent.

Proteinoid microspheres have been used to deliver pharmaceuticals. See, for example, U.S. Pat. Nos. 5,401,516; 5,443,841; and Re. 35,862. In addition, certain modified amino acids have been used to deliver pharmaceuticals. See, for example, U.S. Pat. Nos. 5,629,020; 5,643,957; 5,766,633; 5,776,888; and 5,866,536.

More recently, a polymer has been conjugated to a modified amino acid or a derivative thereof via a linkage group to provide for polymeric delivery agents. The modified polymer may be any polymer, but preferred polymers include, but are not limited to, polyethylene glycol (PEG), and derivatives thereof. See, for example, International Patent Publication No. WO 00/40203.

However, there is still a long-felt need for simple, inexpensive delivery systems which are easily prepared and which can deliver a broad range of active agents by various routes.

SUMMARY OF THE INVENTION

The present invention provides delivery agent compounds comprising a cyclic moiety that are useful to facilitate the delivery of biologically active agents (e.g. pharmaceutically and medicinally useful agents). Delivery agent compounds of the present invention include those having the formula I:

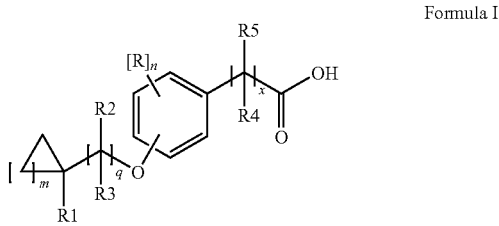

Formula I and pharmaceutically acceptable salts thereof, wherein m is an integer from 1 to 6;

n is an integer from 0 to 4;

q and x are integers independently chosen from zero to 10;

R may be the same or different and is selected from hydrogen, halogen, a substituted or non-substituted alkyl, substituted or non-substituted alkyloxyl, substituted or non-substituted alkenyloxyl, substituted or non-substituted alkynyloxyl and substituted or non-substituted aryloxyl; and R1, R2, R3, R4 and R5 are independently selected from hydrogen, halogen, substituted or non-substituted alkyl, substituted or non-substituted alkenyl, substituted or non-substituted alkynyl, substituted or non-substituted alkyloxyl, substituted or non-substituted aryloxyl, substituted or non-substituted aryl groups, substituted or non-substituted heteroaryl, substituted or non-substituted cycloalkyl, and substituted or non-substituted heterocycloalkyl groups.

According to one preferred embodiment, R1, R2, R3, R4 and R5 are hydrogen; m is 1 to 4; n and x are zero; q is zero to 1, R is hydrogen, a substituted or non-substituted alkoxyl, or substituted or non-substituted aryloxyl. In a further embodiment R is hydrogen, or a substituted or non-substituted $C_1$-$C_6$ alkoxyl.

According to another preferred embodiment, R1, R2, R3, R4 and R5 are hydrogen; m is 3; n, x, and q are zero; R is hydrogen, a substituted or non-substituted alkoxyl, or substituted or non-substituted aryloxyl. In a further embodiment, R is hydrogen; or a substituted or non-substituted $C_1$-$C_6$ alkoxyl.

According to another preferred embodiment, R1, R2, R3, R4 and R5 are hydrogen; m is 1 to 4; n, x, and q are 1; and R is methoxyl.

According to another preferred embodiment, R1, R2, R3, R4 and R5 are hydrogen; m is 1 to 4; n and x are 1; and q is zero; and R is methoxyl.

According to another preferred embodiment, R, R1, R2, R3, R4 and R5 are hydrogen; m is 1 to 4; n and x are zero; and q is zero to 1.

According to another preferred embodiment, R, R1, R2, R3, R4 and R5 are hydrogen; m is 1 to 4; n is zero; x is 1, and q is zero to 1.

According to another preferred embodiment, R, R1, R2, R3, R4 and R5 are hydrogen; m is 1 to 4; n is zero; x is 2; and q is zero to 1.

Mixtures of the delivery agent compounds of the present invention and other delivery agent compounds may also be used.

The invention also provides a pharmaceutical composition comprising at least one delivery agent compound of the present invention, and at least one active agent. These compositions deliver active agents to selected biological systems in increased or improved bioavailability of the active agent compared to administration of the active agent without the delivery agent compound.

Also provided is a dosage unit form comprising a pharmaceutical composition of the present invention. The dosage unit form may be in the form of a liquid or a solid, such as a tablet, capsule or particle, including a powder or sachet.

Another embodiment is a method for administering an active agent to an animal, particularly an animal in need of the active agent, by administering a pharmaceutical composition comprising at least one of delivery agent compound of the present invention and the active agent to the animal. Preferred routes of administration include the oral and intracolonic routes.

Yet another embodiment is a method of treating a disease or for achieving a desired physiological effect in an animal by administering the pharmaceutical composition of the present invention.

Yet another embodiment is a method of preparing a pharmaceutical composition of the present invention by mixing at least one delivery agent compound of the present invention, and at least one active agent.

DETAILED DESCRIPTION OF THE INVENTION

Definitions

The term "alkyl" refers to a straight or branched hydrocarbon chain radical containing no double bonds and having from 1 to 20 carbon atoms, and which is attached to the rest of the molecule by a single bond, e.g., methyl, ethyl, n-propyl, 1-methylethyl (isopropyl), n-butyl, n-pentyl, and 1,1-dimethylethyl (t-butyl).

The term "alkenyl" refers to a straight or branched aliphatic hydrocarbon group containing at least one carbon-carbon double bond having from 2 to about 20 carbon atoms, e.g., ethenyl, 1-propenyl, 2-propenyl (allyl), iso-propenyl, 2-methyl-1-propenyl, 1-butenyl, and 2-butenyl.

The term "alkynyl" refers to a straight or branched chain hydrocarbon group having at least one carbon-carbon triple bond, and from 2 up to about 12 carbon atoms, e.g., ethynyl, propynyl, and butnyl.

The term "alkyloxy" or "alkyloxyl" refers to an alkyl group attached via an oxygen linkage to the rest of the molecule. Representative examples of alkyloxy groups include $OCH_3$, and $-OC_2H_5$.

The term "alkenyloxy" "alkenloxyl" refers to an alkenyl group attached via an oxygen linkage to the rest of the molecule. Representative examples of those groups are $-OCH=CH_2$ and $OC(CH_2)=CH-CH_3$.

The term "alkynyloxy" or "alkynyloxyl" refers to an alkynyl group attached to the rest of the molecule via an oxygen linkage.

The term "aryl" refers to an aromatic radical having 6 to 14 carbon atoms. Representative examples of aryl groups include phenyl, naphthyl, tetrahydronapthyl, indanyl, and biphenyl.

The term "aryloxy" or "aryloxyl" refers to an aryl group attached via an oxygen linkage to the rest of the molecule. Representative examples of those groups are $-O-C_6H_5$ and $-O$-naphthyl.

The term "cycloalkyl" refers to a non-aromatic mono or multicyclic ring system of 3 to 12 carbon atoms. Non-limiting examples of cycloalkyl groups include cyclopropyl, cyclobutyl, cyclopentyl, and cyclohexyl.

Unless otherwise specified, the term "substituted" as used herein refers to substitution with any one or any combination of the following substituents: hydroxy, $C_1$-$C_4$ alkyl, aryl, methyl, ethyl, propyl, isopropyl, normal or iso-butyl, alkoxy, or aryloxy.

The term "multiply interrupted" refers to between 2 and 10 interruptions in a chain where each interruption can be independently before, after, or between any other bond along the chain and may occur in any order or combination.

Delivery Agent Compounds

The delivery agent compounds of the present application may be in the form of the free base or pharmaceutically acceptable salts thereof, such as pharmaceutically acceptable acid addition salts. Suitable salts include, but are not limited to, organic and inorganic salts, for example ammonium, acetate salt, citrate salt, halide (preferably hydrochloride), hydroxide, sulfate, nitrate, phosphate, alkoxy, perchlorate, tetrafluoroborate, carboxylate, mesylate, fumerate, malonate, succinate, tartrate, acetate, gluconate, and maleate. Preferred salts include, but are not limited to, citrate, tosylate, and mesylate salts. The salts may also be solvates, including ethanol solvates, and hydrates.

Salts of the delivery agent compounds of the present invention may be prepared by methods known in the art. For example, citrate salts and mesylate salts may be prepared in ethanol, toluene and citric acid.

The delivery agent compound may be purified by recrystallization or by fractionation on one or more solid chromatographic supports, alone or linked in tandem. Suitable recrystallization solvent systems include, but are not limited to, ethanol, water, heptane, ethyl acetate, acetonitrile, acetone, methanol, and tetrahydrofuran (THF) and mixtures thereof. Fractionation may be performed on a suitable chromatographic support such as alumina, using methanol/n-propanol mixtures as the mobile phase; reverse phase chromatography using trifluoroacetic acid/acetonitrile mixtures as the mobile phase; and ion exchange chromatography using water or an appropriate buffer as the mobile phase. When anion exchange chromatography is performed, preferably a 0-500 mM sodium chloride gradient is employed.

The delivery agent may contain a polymer conjugated to it by a linkage group selected from the group consisting of —NHC(O)NH—, —C(O)NH—, —NHC(O), —OOC—, —COO—, —NHC(O)O—, —OC(O)NH—, —CH$_2$NH—, —NHCH$_2$—, —CH$_2$NHC(O)O—, —OC(O)NHCH$_2$—, —CH$_2$NHCOCH$_2$O—, —OCH$_2$C(O)NHCH$_2$—, —NHC(O)CH$_2$O—, —OCH$_2$C(O)NH—, —NH—, —O—, and carbon-carbon bond, with the proviso that the polymeric delivery agent is not a polypeptide or polyamino acid. The polymer may be any polymer including, but not limited to, alternating copolymers, block copolymers and random copolymers, which are safe for use in mammals. Preferred polymers include, but are not limited to, polyethylene; polyacrylates; polymethacrylates; poly(oxyethylene); poly(propylene); polypropylene glycol; polyethylene glycol (PEG); and derivatives thereof and combinations thereof. The molecular weight of the polymer typically ranges from about 100 to about 200,000 daltons. The molecular weight of the polymer preferably ranges from about 200 to about 10,000 daltons. In one embodiment, the molecular weight of the polymer ranges from about 200 to about 600 daltons and more preferably ranges from about 300 to about 550 daltons.

Non-limiting examples of delivery agent compounds of formula I include those shown below and pharmaceutically acceptable salts thereof:

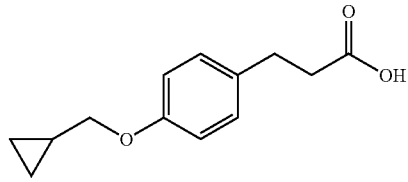 [SMILES: O=C(O)CCc1ccc(OCC2CC2)cc1]

Compound (1): 3-[4-(cyclopropylmethoxy)phenyl]propanoic acid;

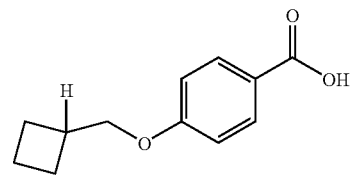 [SMILES: O=C(O)c1ccc(OCC2CCC2)cc1]

Compound (2): 4-(cyclobutylmethoxy)benzoic acid;

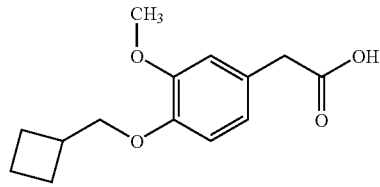 [SMILES: COc1cc(CC(=O)O)ccc1OCC1CCC1]

Compound (3): [4-(cyclobutylmethoxy)-3-methoxyphenyl] acetic acid;

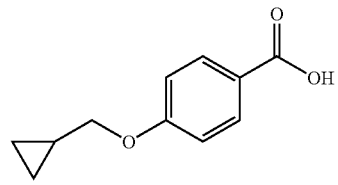 [SMILES: O=C(O)c1ccc(OCC2CC2)cc1]

Compound (4): 4-(cyclopropylmethoxy)benzoic acid;

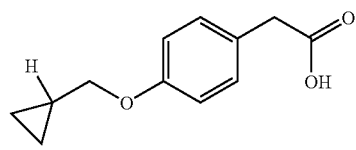 [SMILES: O=C(O)Cc1ccc(OCC2CC2)cc1]

Compound (5): [4-(cyclopropylmethoxy)phenyl]acetic acid;

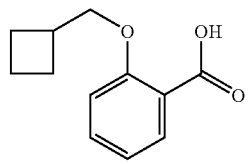 [SMILES: O=C(O)c1ccccc1OCC1CCC1]

Compound (6): 2-(cyclobutylmethoxy)benzoic acid;

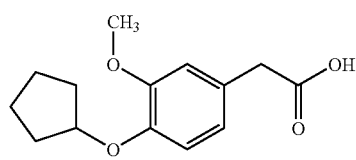 [SMILES: COc1cc(CC(=O)O)ccc1OC1CCCC1]

Compound (7): [4-(cyclopentyloxy)-3-methoxyphenyl]acetic acid;

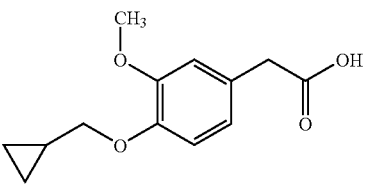 [SMILES: COc1cc(CC(=O)O)ccc1OCC1CC1]

Compound (8): [4-(cyclopropylmethoxy)-3-methoxyphenyl] acetic acid;

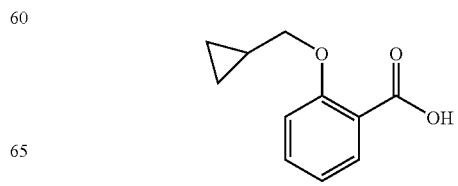

Compound (9): 2-(cyclopropylmethoxy)benzoic acid;

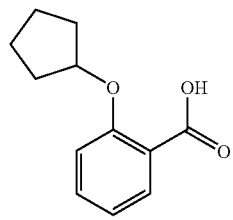 [SMILES: O=C(O)c1ccccc1OC1CCCC1]

Compound (10): 2-(cyclopentyloxy)benzoic acid;

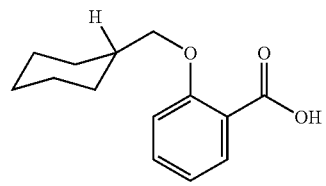 [SMILES: O=C(O)c1ccccc1OCC1CCCCC1]

Compound (11): 2-(cyclohexylmethoxy)benzoic acid;

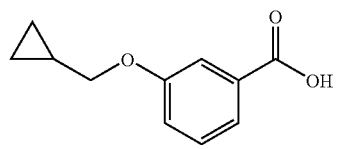 [SMILES: O=C(O)c1cccc(OCC2CC2)c1]

Compound (12): 3-(cyclopropylmethoxy)benzoic acid;

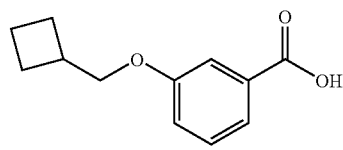 [SMILES: O=C(O)c1cccc(OCC2CCC2)c1]

Compound (13): 3-(cyclobutylmethoxy)benzoic acid;

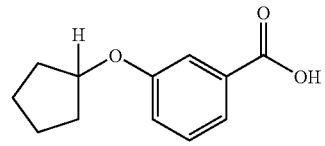 [SMILES: O=C(O)c1cccc(OC2CCCC2)c1]

Compound (14): 3-(cyclopentyloxy)benzoic acid;

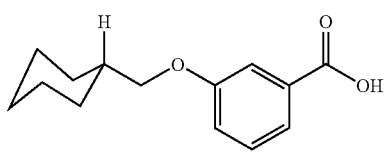 [SMILES: O=C(O)c1cccc(OCC2CCCCC2)c1]

Compound (15): 3-(cyclohexylmethoxy)benzoic acid;

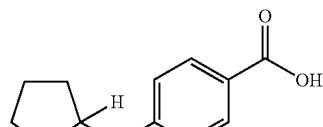

Compound (16): 4-(cyclopentyloxy)benzoic acid;

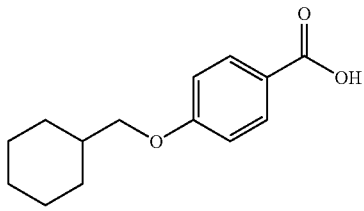 [SMILES: O=C(O)c1ccc(OCC2CCCCC2)cc1]

Compound (17): 4-(cyclopentyloxy)benzoic acid;

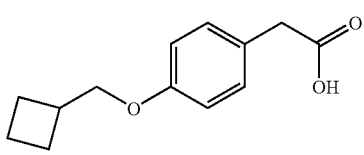 [SMILES: O=C(O)Cc1ccc(OCC2CCC2)cc1]

Compound (18): [4-(cyclobutylmethoxy)phenyl]acetic acid;

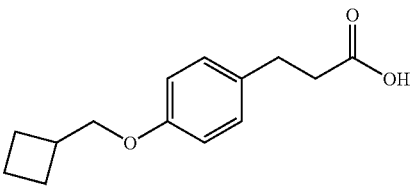 [SMILES: O=C(O)CCc1ccc(OCC2CCC2)cc1]

Compound (19): 3-[4-(cyclobutylmethoxy)phenyl]propanoic acid;

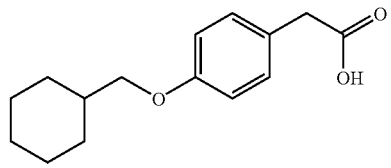 [SMILES: O=C(O)Cc1ccc(OCC2CCCCC2)cc1]

Compound (20): [4-(cyclohexylmethoxy)phenyl]acetic acid;

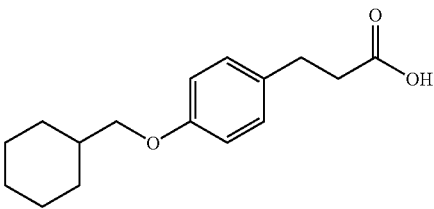 [SMILES: O=C(O)CCc1ccc(OCC2CCCCC2)cc1]

Compound (21): 3-[4-(cyclohexylmethoxy)phenyl]propanoic acid;

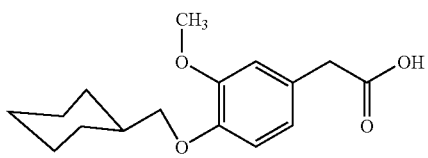 [SMILES: COc1cc(CC(=O)O)ccc1OCC1CCCCC1]

Compound (22): [4-(cyclohexylmethoxy)-3-methoxyphenyl]acetic acid;

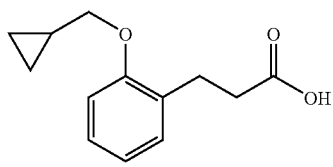

Compound (23): 3-[2-(cyclopropylmethoxy)phenyl]propanoic acid;

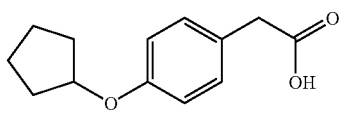 [SMILES: O=C(O)Cc1ccc(OC2CCCC2)cc1]

Compound (24): [4-(cyclopentyloxy)phenyl]acetic acid;

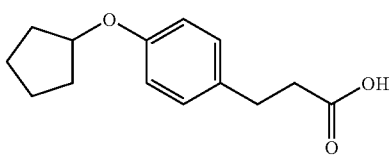 [SMILES: O=C(O)CCc1ccc(OC2CCCC2)cc1]

Compound (25): 3-[4-(cyclopentyloxy)phenyl]propanoic acid.

Active Agents

Active agents suitable for use in the present invention include biologically active agents and chemically active agents, including, but not limited to, pesticides, pharmacological agents, and therapeutic agents. Suitable active agents include those that are rendered less effective, ineffective or are destroyed in the gastro-intestinal tract by acid hydrolysis, enzymes and the like. Also included as suitable active agents are those macromolecular agents whose physiochemical characteristics, such as, size, structure or charge, prohibit or impede absorption when dosed orally.

For example, biologically or chemically active agents suitable for use in the present invention include, but are not limited to, proteins; polypeptides; peptides; hormones; polysaccharides, and particularly mixtures of muco-polysaccharides; carbohydrates; lipids; small polar organic molecules (i.e. polar organic molecules having a molecular weight of 500 daltons or less); other organic compounds; and particularly compounds which by themselves do not pass (or which pass only a fraction of the administered dose) through the gastro-intestinal mucosa and/or are susceptible to chemical cleavage by acids and enzymes in the gastro-intestinal tract; or any combination thereof.

Further examples include, but are not limited to, the following, including synthetic, natural or recombinant sources thereof: growth hormones, including human growth hormones (hGH), recombinant human growth hormones (rhGH), bovine growth hormones, and porcine growth hormones; growth hormone releasing hormones; growth hormone releasing factor, interferons, including α (e.g., interferon alfacon-1 (available as Infergen® from InterMune, Inc. of Brisbane, Calif.)), β and γ; interleukin-1; interleukin-2; insulin, including porcine, bovine, human, and human recombinant, optionally having counter ions including zinc, sodium, calcium and ammonium; insulin-like growth factor, including IGF-1; heparin, including unfractionated heparin, heparinoids, dermatans, chondroitins, low molecular weight heparin, very low molecular weight heparin and ultra low molecular weight heparin; calcitonin, including salmon, eel, porcine and human; erythropoietin; atrial naturetic factor; antigens; monoclonal antibodies; somatostatin; protease inhibitors; adrenocorticotropin, gonadotropin releasing hormone; oxytocin; leutinizing-hormone-releasing-hormone; follicle stimulating hormone; glucocerebrosidase; thrombopoietin; filgrastim; prostaglandins; cyclosporin; vasopressin; cromolyn sodium (sodium or disodium chromoglycate); vancomycin; desferrioxamine (DFO); bisphosphonates, including alendronate, tiludronate, etidronate, clodronate, pamidronate, olpadronate, and incadronate; parathyroid hormone (PTH), including its fragments; anti-migraine agents such as BIBN-4096BS and other calcitonin gene-related proteins antagonists; glucagon-like peptide 1 (GLP-1); Argatroban; antimicrobials, including antibiotics, anti-bacterials and anti-fungal agents; vitamins; analogs, fragments, mimetics or polyethylene glycol (PEG)-modified derivatives of these compounds; or any combination thereof. Non-limiting examples of antibiotics include gram-positive acting, bacteriocidal, lipopeptidal and cyclic peptidal antibiotics, such as daptomycin and analogs thereof.

Delivery Systems

The pharmaceutical composition of the present invention comprises one or more delivery agent compounds of the present invention, and one or more active agents. In one embodiment, one or more of the delivery agent compounds, or salts of these compounds, may be used as a delivery agent by mixing with the active agent prior to administration to form an administration composition.

The administration compositions may be in the form of a liquid. The solution medium may be water (for example, for salmon calcitonin, parathyroid hormone, and erythropoietin), 25% aqueous propylene glycol (for example, for heparin) and phosphate buffer (for example, for rhGH). Other dosing vehicles include polyethylene glycol. Dosing solutions may be prepared by mixing a solution of the delivery agent compound with a solution of the active agent, just prior to administration. Alternately, a solution of the delivery agent compound (or active agent) may be mixed with the solid form of the active agent (or delivery agent compound). The delivery agent compound and the active agent may also be mixed as dry powders. The delivery agent compound and the active agent can also be admixed during the manufacturing process.

The dosing solutions may optionally contain additives such as phosphate buffer salts, citric acid, glycols, or other dispersing agents. Stabilizing additives may be incorporated into the solution, preferably at a concentration ranging between about 0.1 and 20% (w/v).

The administration compositions may alternately be in the form of a solid, such as a tablet, capsule or particle, such as a powder or sachet. Solid dosage forms may be prepared by mixing the solid form of the compound with the solid form of the active agent. Alternately, a solid may be obtained from a solution of compound and active agent by methods known in the art, such as freeze-drying (lyophilization), precipitation, crystallization and solid dispersion.

The administration compositions of the present invention may also include one or more enzyme inhibitors. Such enzyme inhibitors include, but are not limited to, compounds such as actinonin or epiactinonin and derivatives thereof. Other enzyme inhibitors include, but are not limited to, aprotinin (Trasylol) and Bowman-Birk inhibitor.

The amount of active agent used in an administration composition of the present invention is an amount effective to accomplish the purpose of the particular active agent for the target indication. The amount of active agent in the compositions typically is a pharmacologically, biologically, therapeutically, or chemically effective amount. However, the amount can be less than that amount when the composition is used in a dosage unit form because the dosage unit form may contain a plurality of delivery agent compound/active agent compositions or may contain a divided pharmacologically, biologically, therapeutically, or chemically effective amount. The total effective amount can then be administered in cumulative units containing, in total, an effective amount of the active agent.

Generally, the amount of delivery agent compound in the composition is an amount effective to facilitate delivery of the active agent. The total amount of active agent and delivery agent to be used can be determined by methods known to those skilled in the art. However, because the compositions of the invention may deliver active agents more efficiently than compositions containing the active agent alone, lower amounts of biologically or chemically active agents than those used in prior dosage unit forms or delivery systems can be administered to the subject, while still achieving the same blood levels and/or therapeutic effects. Generally, the weight ratio of delivery agent to active agent ranges from about 800:1 to about 10:1, and preferably ranges from about 400:1 to about 100:1. Other ranges are contemplated to be within acceptable ranges for delivery of some active compounds, such as from about 100:1 to about 2.5:1, or from about 60:1 to about 1:1. Such ranges and ratios can be determined by one skilled in the art.

The presently disclosed delivery agent compounds facilitate the delivery of biologically and chemically active agents, particularly in oral, intranasal, sublingual, intraduodenal, subcutaneous, buccal, intracolonic, rectal, vaginal, mucosal, pulmonary, transdermal, intradermal, parenteral, intravenous, intramuscular and ocular systems, as well as traversing the blood-brain barrier.

Dosage unit forms can also include any one or combination of excipients, diluents, disintegrants, lubricants, plasticizers, colorants, flavorants, taste-masking agents, sugars, sweeteners, salts, and dosing vehicles, including, but not limited to, water, 1,2-propane diol, ethanol, olive oil, or any combination thereof.

The compounds and compositions of the subject invention are useful for administering biologically or chemically active agents to any animals, including but not limited to birds such as chickens; mammals, such as rodents, cows, pigs, dogs, cats, primates, and particularly humans; and insects.

The system is particularly advantageous for delivering chemically or biologically active agents that would otherwise be destroyed or rendered less effective by conditions encountered before the active agent reaches its target zone (i.e. the area in which the active agent of the delivery composition is to be released) and within the body of the animal to which they are administered. Particularly, the compounds and compositions of the present invention are useful for orally administering active agents, especially those that are not ordinarily orally deliverable, or those for which improved delivery is desired.

The compositions comprising the compounds and active agents have utility in the delivery of active agents to selected biological systems and in an increased or improved bioavailability of the active agent compared to administration of the active agent without the delivery agent. Delivery can be improved by delivering more active agent over a period of time, or in delivering the active agent in a particular time period (such as to effect quicker or delayed delivery), or in delivering the active agent at a specific time, or over a period of time (such as sustained delivery).

Another embodiment of the present invention is a method for the treatment or prevention of a disease or for achieving a desired physiological effect, such as those listed in the table below, in an animal by administering the composition of the present invention. Preferably, an effective amount of the composition for the treatment or prevention of the desired disease or for achieving the desired physiological effect is administered. Specific indications for active agents can be found in the Physicians' Desk Reference (54th Ed., 2000, Medical Economics Company, Inc., Montvale, N.J.), which is herein incorporated by reference. The active agents in the table below include their analogs, fragments, mimetics, and polyethylene glycol-modified derivatives.

| Active Agent | Disease and Physiological Effect |
| --- | --- |
| Growth hormones (including human recombinant growth hormone and growth-hormone releasing factors and its analogs) | Growth disorders |
| Interferons, including $\alpha$, $\beta$ and $\gamma$ | Viral infection, including chronic cancer, hepatitis, and multiple sclerosis |
| Interleukins (e.g. Interleukin-1; interleukin-2) | Viral infection; cancer; cell mediated immunity; and transplant rejection; |
| Insulin; Insulin-like growth factor IGF-1 | Diabetes |
| Immune Globulins, such as IVIg | smallpox, rabies, and diphtheria, Alzheimer's Disease; Primary immunodeficiencies; Acute Guillain-Barré syndrome; Chronic idiopathic demyelinating polyneuropathy (CIDP); Myasthenia gravis, polymyositis, and dermatomyositis; neonatal immune thrombocytopenia, heparin-induced thrombocytopenia, and antiphospholipid antibody syndrome: Posttransfusion purpura. |

-continued

| Active Agent | Disease and Physiological Effect |
|---|---|
| Heparin; Low Molecular Weight Heparin | Treatment and Prevention of Thrombosis, including (Deep Vein Thrombosis); prevention of blood coagulation |
| Calcitonin; salmon calcitonin | Osteoporosis; diseases of the bone; bone pain; analgesic (including pain associated with osteoporosis or cancer) |
| Erythropoietin alpha, Erythropoietin beta, Pegylated erythropoietin; darbepoietin alpha, or combinations thereof. | Anemia; HIV/HIV-therapy Associated Anemia; Chemotherapeutically-Induced Anemia |
| Atrial naturetic factor | Vasodilation |
| Antigens | Infection |
| CPHPC Amyloid Scavengers (from list of last application) | Reduction of amyloid deposits and systemic amyloidoisis often (but not always) in connection with Alzheimer's disease, Type II diabetes, and other amyloid-based diseases |
| Monoclonal antibodies | To prevent graft rejection; cancer; used in assays to detect diseases |
| Somatostatin/octreotide | Bleeding ulcer; erosive gastritis; variceal bleeding; diarrhea; acromegaly; TSH-secreting pituitary adenomas; secretory pancreatic tumors; carcinoid syndrome; reduce proptosis/thyroid-associated ophthalmopathy; reduce macular edema/retinopathy |
| Protease inhibitors | HIV Infection/AIDS |
| Adrenocorticotropin | High cholesterol (to lower cholesterol) |
| Gonadotropin releasing hormone | Ovulatory disfunction (to stimulate ovulation) |
| Oxytocin | Labor disfunction (to stimulate contractions) |
| Leutinizing-hormone-releasing-hormone; Leutinizing Hormone; follicle stimulating hormone | Regulate reproductive function |
| Glucocerebrosidase | Gaucher disease (to metabolize lipoprotein) |
| Thrombopoietin | Thrombocytopenia |
| Filgrastim (Granulocyte Colony Stimulating Factor); GM-CSF, (sargramostim) and their Pegylated forms | shorten the duration of chemotherapy-induced neutropenia and thus treat or prevent infection in chemotherapy patients; Inhibit the growth of or to kill *Mycobacterium* Intracellular Avium Infection (MAC) |
| RNAi | Huntington, Alzheimers, Viral Infections (HIV, Hepatitis A, B or C, RSV), Cancers; Macular Degeneration |
| Prostaglandins | Hypertension |
| Cyclosporin | Transplant rejection; psoriasis, inflammatory alopecias; Sjogren's syndrome; Keratoconjunctivitis Sicca |
| Vasopressin | Nocturnal Enuresis; antidiuretic |
| Cromolyn sodium; | Asthma; allergies |
| Vancomycin | Treat or prevent antimicrobial-induced infections including, but not limitted to methacillin-resistant *Staphalococcus aureus* and *Staph. epidermiditis* |
| APO1 (FAS gene) | encodes one of several proteins important to apoptosis, the normal process through which cells die. Mutations in the FAS gene have been found in ALPS (the autoimmune lymphoproliferative syndrome); autoimmune disorders; cancer T |
| Recombinant Hepatitis A, B or C Vaccines (e.g. purified HBsAG produced without CsCl) | Confer immunity to Hepatitis viruses |
| Typhoid Vaccine (e.g. Vi polysaccharide of the Ty2 strain). | Confer immunity to *S. typhi* or other Typhoid bacilli |
| Parathyroid hormone (PTH), including its fragments. | Osteoporosis; Diseases of the bone |
| Antimicrobials | Infection including but not limited to gram-positive bacterial infection |
| Vitamins | Treat and prevent Vitamin deficiencies |
| Bisphosphonates | Osteoporosis; Paget's disease; bone tumors and metastases (and associated pain); Breast cancer; including as adjuvant therapy for early stage breast cancer; management of bone metastases (and associated pain), including bone metastases associate with breast cancer, prostate cancer, and lung cancer; Inhibits osteoclasts; Promotes osteoblastic activity; treat and/or prevent bone mineral density (bmd) loss; multiple myeloma; prevention of bone complications related to malignant osteolysis; fibrous dysplasia; pediatric osteogenesis imperfecta; hypercalcemia, urethral (urinary tract) |

-continued

| Active Agent | Disease and Physiological Effect |
|---|---|
| | malignancies; reflex sympathetic dystropy synodrome, acute back pain after vertebral crush fracture, chronic inflammatory joint disease, renal bone disease, extrosseous calcifications, analgesic, vitamin D intoxication, periarticular ossifications |
| BIBN4096BS - (1-Piperidinecarboxamide. N-[2-[[5-amino-1-[[4-(4-pyridinyl)-1-piperazinyl)carbonyl]pentyl]amino]-1-[(3,5-dibromo-4-hydroxyphenyl)methyl]-2-oxoethyl]-4(1,4-dihydro-2-oxo-3(2H0-quinazolinyl)-.[R-(R*,S*)]-) | Anti-migraine; calcitonin gene-related peptide antagonist |
| Glucagon | improving glycemic control (e.g. treating hypoglycemia and controlling hypoglycemic reactions), obesity; a diagnostic aid in the radiogical examination of the stomach, duodenum, small bowel and colon; Treat acute poisoning With Cardiovascular Agents including, but not limited to, calcium channel blockers, beta blockers |
| GLP-1, Exendin-3, Exendin-4, Obestatin; MCHR1 receptor antagonists; selective inhibitor of 11-beta hydroxysteroid dehydrogenase type 1 | Diabetes; improving glycemic control (e.g. treating hypoglycemia and controlling hypoglycemic reactions), obesity |
| dipeptidyl peptidase IV (DPP-4) inhibitors | Diabetes; improving glycemic control (e.g. treating hypoglycemia), obesity |
| Acyclovir, valacyclovir | Used to treat herpes infections of the skin, lip and genitals; herpes zoster (shingles); and chickenpox |
| HIV Entry Inhibitors (e.g. Fuzeon) | Inhibit entry of HIV into host cells |
| Sumatriptin, almotriptan, naratriptan, rizatriptan, frovatriptan and eletriptan (piperidinyloxy)phenyl, (piperidinyloxy)pyridinyl, (piperidinylsulfanyl)phenyl and (piperidinylsulfanyl)pyridinyl compounds | anti-migraine serotonin agonists |
| Neuraminidase inhibitors: peramivir, zanamivir, oseltamivir, BCX-1898, BCX-1827, BCX-1989, BCX 1923, BCX 1827 and A315675; M2 inhibitors: amantadine, rimantadine; Nucleoside/Nucleotide Reverse Transcriptase Inhibitors, Non-nucleoside Reverse Transcriptase Inhibitors, Protease Inhibitors, Fusion inhibitors: thiovir, thiophosphonoformate, foscarnet, enfuviritide, zidovudine, didanosine, zalcitabine, stavudine, lamivudine, emtricitabine, abacavir, azidothymidine, tenofovir disoproxil, delavridine, efavirenz, nevirapine, ritonavir, nelfinavir mesylate, saquinvir mesylate, indinavir sulfate, amprenavir, lopinavir, lopinavir, fosamprenavir calcium, atazanavir sulfate | Antivirals for the treatment of, for example, influenza or HIV/AIDS |
| Peptide YY (PYY) and PYY-like Peptides (e.g. PYY[3-36]) | Obesity, Diabetes, Eating Disorders, Insulin-Resistance Syndromes |
| APO a-I Mimetics (e.g. APPO18) | Increase HDL; reduce vascular atherosclerotic plaque formation and accumulation. |
| Clotting factors, such as Factor IX and X | Hemophilia |

For example, one embodiment of the present invention is a method for treating a patient suffering from or susceptible to diabetes by administering insulin and at least one of the delivery agent compounds of the present invention.

Following administration, the active agent present in the composition or dosage unit form is taken up into the circulation. The bioavailability of the agent can be readily assessed by measuring a known pharmacological activity in blood, e.g. an increase in blood clotting time caused by heparin, or a decrease in circulating calcium levels caused by calcitonin. Alternately, the circulating levels of the active agent itself can be measured directly.

EXAMPLES

The following examples illustrate the present invention without limitation.

Example 1

Synthesis of Delivery Agent Compounds

Analytical HPLC were conducted utilizing Perkin-Elmer's Series 200 auto sampler and pump with either a Perkin-Elmer series 200 or Applied Biosystems 785A UV/Vis detector (both monitoring at $\lambda=220$ nm). Phenomenex's Kromasil 5 micron C18 column (50 mm×4.6 mm) fitted with Phenomenex's C18 (ODS, Octadecyl) security guard cartridges (4 mm×3 mm) were utilized with a 3 mL/min flow-rate. The solvent system consisted of mixtures of acetonitrile and water, containing 0.1% (v/v) trifluoroacetic acid, with the gradient starting at 5% acetonitrile and increasing to 95% over 10.5 minutes.

Gas chromatographic analyses were performed on a Agilant 6890N GC system equipped with a 30-m 5% polyphenyl methyl siloxane capillary column (0.32 mm i.d.). Helium was used as the carrier gas, and the flow rate was kept constant at 7.7 mL/min. The retention time was measured under the following conditions: injector temperature: 250° C.; initial temperature of the column: 150° C.; increment rate 8° C./min to 200° C. After being kept at 200° C. for 8.0 min, the temperature was raised to 290° C. at an increment rate 8° C./min.

All reactions reported in this invention were carried in oven-dried three-necked, round-bottomed flasks equipped with a Teflon-coated magnetic stirring bar. The reaction flask was purged with nitrogen, and during the entire operation, the reaction was under nitrogen. The representative synthetic methods for preparing are set forth in the following examples.

Delivery Agent 1:
3-[4-(cyclopropylmethoxy)phenyl]propanoic Acid

To a stirred solution of methyl 4-hydroxyphenylpropanoate (2.41 g, 13.4 mmol) and potassium carbonate (2.76 g, 20 mmol) in 75 mL of 2-butanone at ambient temperature was added in one portion of (bromomethyl)cyclopropane (2.72 g, 20 mmol). The stirred reaction mixture was heated at reflux for 18 hr. HPLC revealed the disappearance of the starting material of methyl 4-hydroxyphenylpropanoate. The mixture was allowed to cool to ambient temperature. The solid was filtered off. The filter cake was washed with acetone. The combined filtrate was concentrated in vacuo to nearly dryness. Methanol was added (10 mL) was added to the residue, followed by the addition of a 2-N aqueous solution of NaOH (25 mL, 50 mmol). The reaction was stirred overnight at about 40° C. HPLC indicated that the saponification was completed, and revealed one single peak signal of the expected carboxylic acid. The reaction mixture was subjected to roto-vaporation to remove methanol. Ice was added to the basic aqueous solution. The acidification with a 30 mL of HCl aqueous 2N solution (60 mmol) led to the immediate precipitation of a white solid. Stirring was continued for an additional 30 min and then the precipitation was filtered off with suction through a sintered glass funnel. The collected solid was successively washed with three 50-mL portions of water, and two 25-mL portions of hexane. The collected solid was dried in vacuo for two days at ambient temperature to afford 1.77 g (60%) of 3-[4-(cyclopropylmethoxy)phenyl]propanoic acid as a white solid.

HPLC: $R_t$: 4.89 min. $^1$H NMR (400 MHz DMSO-6): δ 0.22 (m, 2H), 0.48 (m, 2H), 1.09 (m, 1H), 2.41 (m, 2H), 2.63 (m, 2H), 3.67 (m, 2H), 6.74 (d, 2H), 7.01 (d, 2H, 11.98 (s, 1H). $^{13}$C NMR (100 MHz DMSO-d6): δ 3.04, 10.17, 29.60, 35.80, 71.87, 114.24, 129.11, 132.56, 156.93, 173.78. LC/MS m/z: 221 [(M+1)$^+$].

Delivery Agent 2: 4-(cyclobutylmethoxy)benzoic Acid

To a stirred solution of ethyl 4-hydroxybenzoate (2.493 g, 15.0 mmol) and potassium carbonate (4.15 g, 30 mmol) in 60 mL of 2-butanone at ambient temperature was added in one portion of (bromomethyl)cyclobutane (97% pure) (2.53 g, 16.5 mmol). The stirred reaction mixture was heated at reflux for 16 hr. HPLC revealed the disappearance of the starting material of ethyl 4-hydroxybenzoate. The mixture was allowed to cool to ambient temperature. The solid was filtered off. The filter cake was washed with acetone. The combined filtrate was concentrated in vacuo to nearly dryness. Methanol was added (10 mL) was added to the residue, followed by the addition of a 2-N aqueous solution of NaOH (30 mL, 60 mmol). The reaction was stirred overnight at about 40° C. HPLC indicated that the saponification was completed, and revealed one single peak signal of the expected carboxylic acid. The reaction mixture was subjected to roto-vaporation to remove methanol. Ice was added to the basic aqueous solution. The acidification with a 35 mL of HCl aqueous 2N solution (70 mmol) led to the immediate precipitation of a white solid. Stirring was continued for an additional 30 min and then the precipitation was filtered off with suction through a sintered glass funnel. The collected solid was successively washed with three 50-mL portions of water, and two 25-mL portions of hexane. The collected solid was dried in vacuo for two days at ambient temperature to afford 2.63 g (85%) of 4-(cyclobutylmethoxy)benzoic acid as a white solid.

HPLC: $R_t$: 5.45 min. $^1$H NMR (400 MHz DMSO-d6): δ 1.82-1.84 (m, 4H), 2.06 (m, 2H), 2.75 (m, 1H), 4.01 (m, 2H), 6.99 (d, 2H), 7.87 (m, 2H), 12.57 (s, 1H). $^{13}$C NMR (100 MHz DMSO-d6): δ 18.06, 24.29, 33.37, 71.66, 114.22, 122.79, 131.29, 162.40, 166.97. LC/MS m/z: 207 [(M+1)$^+$].

Delivery Agent 3:
4-(cyclobutylmethoxy)-3-methoxyphenyl]acetic Acid

To a stirred solution of ethyl ethyl (4-hydroxy-3-methoxyphenyl)acetate (1.05 g, 5.0 mmol) and potassium carbonate (1.38 g, 10 mmol) in 40 mL of 2-butanone at ambient temperature was added in one portion of (bromomethyl)cyclobutane (97% pure) (1.53 g, 10.0 mmol). The stirred reaction mixture was heated at reflux for 24 hr. HPLC revealed the disappearance of the starting material of ethyl (4-hydroxy-3-methoxyphenyl)acetate. The mixture was allowed to cool to ambient temperature. The solid was filtered off. The filter cake was washed with acetone. The combined filtrate was concentrated in vacuo to nearly dryness. Methanol was added (5 mL) was added to the residue, followed by the addition of a 2-N aqueous solution of NaOH (20 mL, 40 mmol). The reaction was stirred overnight at about 40° C. HPLC indicated that the saponification was completed, and revealed one single peak signal of the expected carboxylic acid. The reaction mixture was subjected to roto-vaporation to remove methanol. Ice was added to the basic aqueous solution. The acidification with a 25 mL of HCl aqueous 2N solution (50 mmol) led to the immediate precipitation of a white solid. Stirring was continued for an additional 30 min and then the precipitation was filtered off with suction through a sintered glass funnel. The collected solid was successively washed with three 50-mL portions of water, and two 25-mL portions of hexane. The collected solid was dried in vacuo for two days at ambient temperature to afford 1.20 g (95%) of [4-(cyclobutylmethoxy)-3-methoxyphenyl]acetic acid as a white solid.

HPLC: $R_t$: 4.87 min $^1$H NMR (400 MHz DMSO-d6): δ 1.78-1.87 (m, 4H), 2.05 (m, 2H), 2.67 (m, 1H), 3.46 (s, 2H), 3.76 (s, 3H), 3.88 (m, 2H), 6.74 (m, 1H), 6.83-6.86 (m, 2H), 12.21 (s, 1H). $^{13}$C NMR (100 MHz DMSO-d6): δ 23.49, 29.84, 39.50, 45.60, 60.93, 77.89, 118.76, 118.99, 126.81, 132.92, 152.48, 154.20, 178.26. LC/MS m/z: 251 [(M+1)$^+$].

This procedure can be repeated, with the appropriate starting materials, and appropriate amounts, to prepare compounds 4-25.

Example 2

Oral Delivery of Insulin in Rats

Human recombinant insulin (ICN Biomedicals, Aurora, Ohio) was dissolved in deionized water (ph ~6.5) to obtain stock insulin solutions having a concentration of 15 mg/ml. 3-[4-(cyclopropylmethoxy)phenyl]propanoic acid (Emisphere Technologies, Tarrytown, N.Y.) was dissolved in deionized water to obtain a 200 mg/ml delivery agent solution. The free acid form of delivery agent as converted to the sodium salt by adding one equivalent of sodium hydroxide. Solutions were vortexted, sonicated, and heated. If necessary, additional sodium hydroxide was added in μl quantities to achieve uniform solubility in the delivery agent solutions. Solutions were adjusted to a pH of 3.5-8.5 by the addition of either hydrochloric acid or sodium hydroxide, as appropriate. The insulin stock solution was then added to the delivery agent solutions to obtain an administration solution ultimately having an insulin concentration of 0.5 mg/ml. After solubilization and drug addition, administration solutions were brought to a final volume by the addition of deionized water.

Insulin was administered to male, Sprague-Dawley rats either alone or in combination with delivery agent by oral gavage (PO). Typically, rats were fasted for 18-24 hours prior to dosing. A Rusch 8 French catheter was cut to 11 cm in length and adapted to fit a 1 ml syringe. The syringe was filled with dosing solution and the catheter was inserted into the rat mouth and fed down the esophagus (10.0 cm). The dosing solution was delivered by pressing the syringe plunger while holding the rat in an upright position. The doses of delivery agent and Insulin were 200 mg/kg and 1 mg/kg, respectively. The dose volume was 1 ml/kg. The weight of the rats in this invention ranges from 250 to 300 grams. The rat was weighted prior to the test and the dose volume was adjusted accordingly.

Immediate to each blood sampling point, rats were exposed briefly (~10 seconds) to carbon dioxide until prostrate. A 77-mm capillary tube was inserted into the retroorbital sinus. Typically, blood samples were collected prior to dosing (time=0) and at 15, 30, 45, and 60 minutes after dosing.

To determine the pharmacodynamic response, a hand-held glucometer (OneTouch Ultra, LifeScan—Johnson & Johnson, New Brunswick, N.J.) was used to measure whole blood glucose after administration of insulin or insulin and delivery agent. After discarding the first drop of blood, a small sample (~5-10 μls) was touched to the glucometer test strip (OneTouch Ultra, LifeScan) and a blood glucose reading was generated by the meter. Typically, samples were collected prior to dosing (time 0) and at 15, 30, 45, and 60 minutes after dosing.

The results for compound (1) are shown in Table 1 below. Table 1 shows the change in blood glucose levels in rats administered insulin (0.5 mg/kg) with delivery agent compounds (1 to 9) (200 mg/kg) at 0, 5, 10, 30, and 60 minutes after administration.

TABLE 1

REDUCTION OF BLOOD GLUCOSE BY INSULIN/DELIVERY AGENT = 0.5 MG/200 MG PER KG AT 0.25 ML SOLUTION DOSE PER RAT

| | Mean Value of the Reduction of Blood Glucose (%) | | | | |
|---|---|---|---|---|---|
| Delivery Agents | 0 | 15 min. | 30 min. | 45 min. | 60 min. |
| Compound 1 | −4.64% | −17.26% | −38.35% | −43.75% | −42.48% |
| Compound 2 | 7.51% | −20.04% | −32.2% | −32.51% | −19.95% |
| Compound 3 | 6.88% | −15.04% | −22.90% | −21.04% | −19.74% |
| Compound 4 | 1.72% | −11.80% | −32.15% | −21.14% | −16.78% |
| Compound 5 | −1.91% | −17.53% | −26.944% | −22.92% | −18.62% |
| Compound 6 | 6.37% | −9.25% | −20.51% | −2.61% | −2.75% |
| Compound 7 | 11.87% | −7.15% | −17.37% | −12.75% | −12.77% |
| Compound 8 | 18.75% | −1.61% | −14.21% | −16.12% | −18.19% |
| Compound 9 | −1.59% | −1.29% | −6.99% | −11.40% | −11.75% |
| Compound 10 | +16.39% | −6.94% | −25.22% | −29.27% | −29.91% |
| Compound 11 | −1.27% | −4.82% | −6.23% | −19.71% | −19.54% |

The above-mentioned patents, applications, test methods, and publications are hereby incorporated by reference in their entirety.

The present invention has been described in details with particular reference to the preferred embodiments thereof, but it will be understood that many variations and modifications of the present invention suggest themselves to those skilled in the art in light of the above detailed description. All such obvious variations and modifications can be affected without departing the spirit and scope of the appended claims of the present invention.

What is claimed is:

1. A compound selected from the group consisting of:

Compound (1):

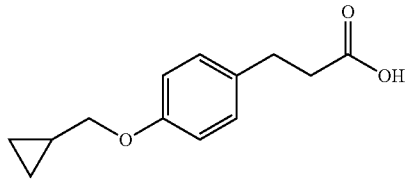

-continued

Compound (3):

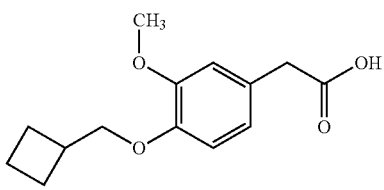

Compound (5):

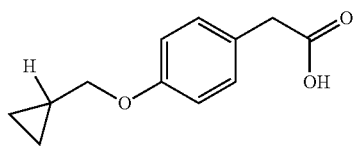

Compound (6):

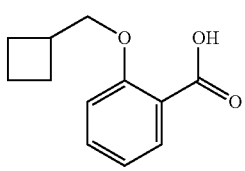

Compound (8):

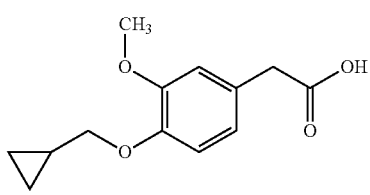

Compound (12):

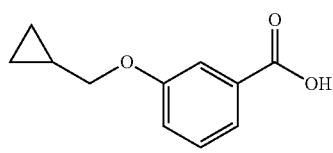

Compound (13):

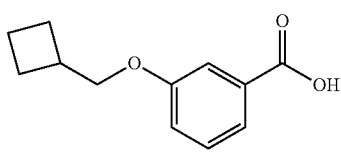

Compound (18):

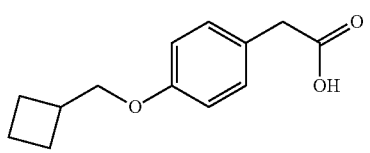

Compound (19):

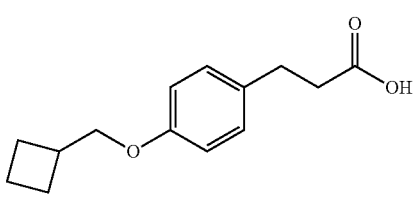

-continued

Compound (23):

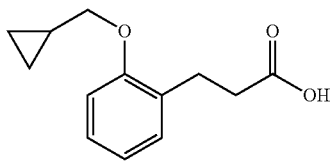

Compound (25):

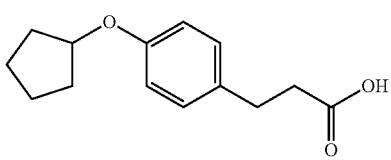

and pharmaceutically acceptable salts thereof.

2. A composition comprising:
   (A) a biologically active agent; and
   (B) at least one compound of claim 1.

3. The composition of claim 2, wherein the biologically active agent comprises at least one protein, polypeptide, peptide, hormone, polysaccharide, mucopolysaccharide, carbohydrate, or lipid.

4. The composition of claim 2, wherein the biologically active agent is selected from the group consisting of: BIBN-4096BS, growth hormones, human growth hormones recombinant human growth hormones (rhGH), bovine growth hormones, porcine growth hormones, growth hormone releasing hormones, growth hormone releasing factor, glucagon, interferons, α-interferon, β-interferon, γ-interferon, interleukin-1, interleukin-2, insulin, porcine insulin, bovine insulin, human insulin, human recombinant insulin, insulin-like growth factor (IGF), IGF-1, heparin, unfractionated heparin, heparinoids, dermatans, chondroitins, low molecular weight heparin, very low molecular weight heparin, ultra low molecular weight heparin, calcitonin, salmon calcitonin, eel calcitonin, human calcitonin; erythropoietin (EPO), atrial naturetic factor, antigens, monoclonal antibodies, somatostatin, protease inhibitors, adrenocorticotropin, gonadotropin releasing hormone, oxytocin, leutinizing-hormone-releasing-hormone, follicle stimulating hormone, glucocerebrosidase, thrombopoeitin, filgrastim, postaglandins, cyclosporin, vasopressin, cromolyn sodium, sodium chromoglycate, disodium chromoglycate, vancomycin, desferrioxamine (DFO), parathyroid hormone (PTH), fragments of PTH, glucagon-like peptide 1 (GLP-1), antimicrobials, anti-fungal agents, vitamins; analogs, fragments, mimetics and polyethylene glycol (PEG)-modified derivatives of these compounds; and any combination thereof.

5. The composition of claim 2, wherein the biologically active agent is selected from insulin, Leutenizing-hormone releasing hormone, GLP-1, heparin, recombinant human growth hormone, glucagon, argatraban, analogs, fragments, mimetics and polyethylene glycol (PEG)-modified derivatives of these compounds; and any combination thereof.

6. The composition of claim 2, wherein the biologically active agent is insulin.

7. A dosage unit form comprising:
   (A) at least one composition of claim 2; and
   (B) (a) an excipient,
       (b) a diluent,
       (c) a disintegrant,
       (d) a lubricant,
       (e) a plasticizer, (f) a colorant, (g) a dosing vehicle, or (h) any combination thereof.

8. A method for administering a biologically-active agent to an animal in need of the agent, the method comprising administering orally to the animal the composition of claim 2.

9. A method for preparing a composition comprising mixing:

(A) at least one biologically active agent;

(B) at least one compound of claim 1; and (C) optionally, a dosing vehicle.

10. A composition comprising a biologically active agent and a compound selected from:

Compound (1)
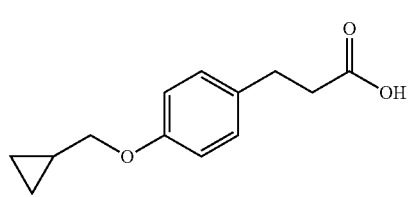

Compound (2)
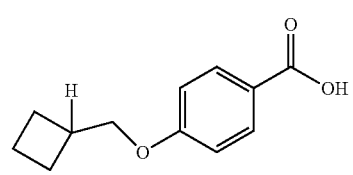

Compound (3)
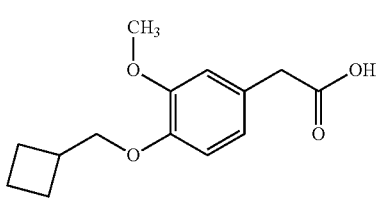

Compound (4)
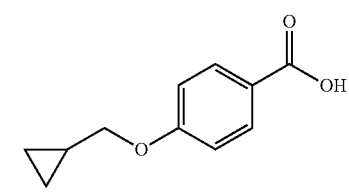

Compound (5)
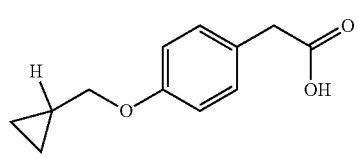

Compound (6)
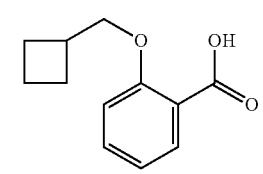

Compound (7)
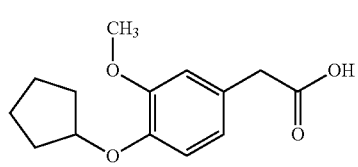

-continued

Compound (8)
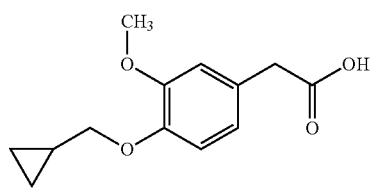

Compound (9)
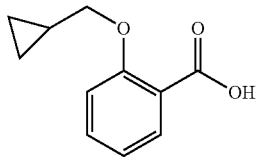

Compound (10)
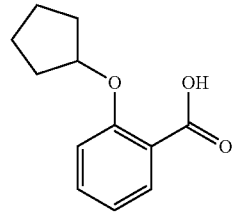

Compound (11)
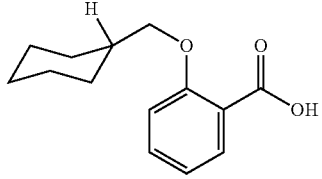

Compound (12)
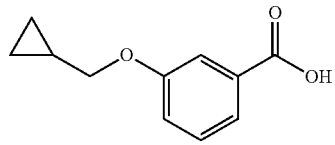

Compound (13)
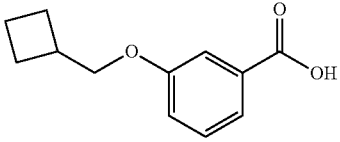

Compound (14)
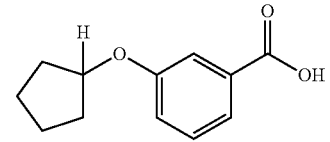

Compound (15)
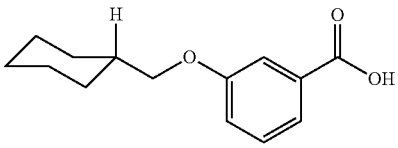

-continued
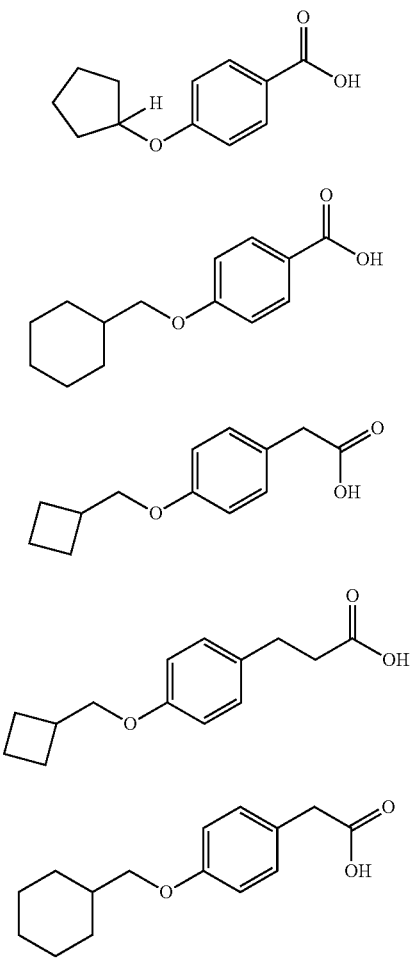
Compound (16)
Compound (17)
Compound (18)
Compound (19)
Compound (20)
-continued
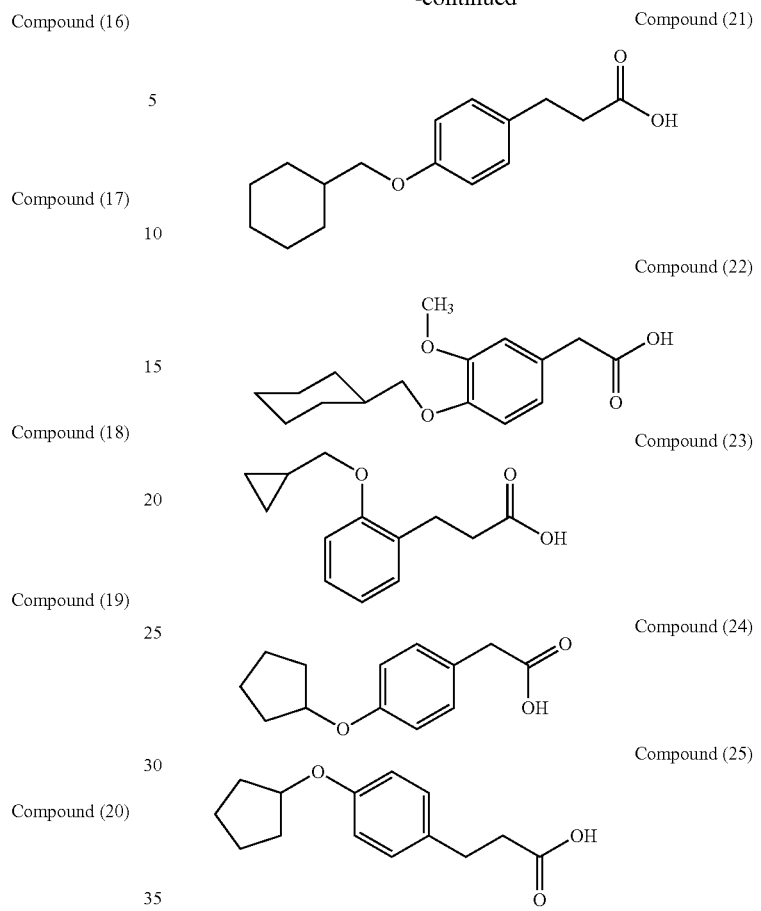
Compound (21)
Compound (22)
Compound (23)
Compound (24)
Compound (25)
and pharmaceutically acceptable salts thereof.
* * * * *